US00PP19253P3

(12) United States Plant Patent
Layt

(10) Patent No.: US PP19,253 P3
(45) Date of Patent: Sep. 23, 2008

(54) *DIANELLA TASMANICA* PLANT NAMED 'DT23'

(50) Latin Name: *Dianella tasmanica*
Varietal Denomination: DT23

(76) Inventor: Todd Anthony Layt, P.O. Box 1011, Richmond NSW 2753 (AU)

( * ) Notice: Subject to any disclaimer, the term of this patent is extended or adjusted under 35 U.S.C. 154(b) by 200 days.

(21) Appl. No.: 11/351,964

(22) Filed: Feb. 10, 2006

(65) Prior Publication Data

US 2006/0185049 P1 Aug. 17, 2006

Related U.S. Application Data

(60) Provisional application No. 60/652,056, filed on Feb. 11, 2005.

(51) Int. Cl.
*A01H 5/00* (2006.01)

(52) U.S. Cl. ..... Plt./424

(58) Field of Classification Search ..... Plt./424, Plt./384, 263
See application file for complete search history.

(56) References Cited

PUBLICATIONS

Layt: "Dianella tasmanica flax lily 'DT23,'" *Plant Varieties Journal* 17 (1): 28, 134,146, 594–596 (Apr. 28, 2004).

*Primary Examiner*—Annette H Para

(57) ABSTRACT

'DT23' is a distinctive variety of *Dianella tasmanica,* which is characterized by its combination of compact form, green leaf color, broad leaf width, strong leaf arching, green summer basal sheath color with red-brown margin, and large bluish-purple berries.

2 Drawing Sheets

Latin name of the genus and species: The Latin name of the novel variety disclosed herein is *Dianella tasmanica* 'DT23'.

Variety denomination:

The inventive variety of *Dianella tasmanica* disclosed herein has been given the variety denomination 'DT23'.

BACKGROUND OF THE INVENTION

The present invention relates to a new and distinct variety of evergreen perennial *Dianella tasmanica,* which has been named 'DT23'. It is anticipated that the plant of this invention will be marketed under the tradename Emerald Arch. *Dianella* are a genus of ornamental grass-like plants in the Phormiaceae family. In general, *Dianella tasmanica* has flax-like leaves. Pale blue flowers on stems up to 40 cm high typically develop in spring and early summer and are followed by green berries that become bluish-purple.

Lineage: The cultivar 'DT23' was discovered in 1996 in Clarendon, New South Wales, Australia, during a seedling selection of cultivated *Dianella tasmanica.* The new variety originated from open pollinated parent plants and subsequent selection of a distinctive seedling from the resulting progeny as part of a breeding program. The breeding program used assisted open pollination with occasional shaking of inflorescences to promote pollen transfer. The parent (*D. tasmanica,* ecotype from southern tablelands of new South Wales, Australia) is characterized by green leaf color, medium leaf width, medium leaf arching, absent to very weak leaf glaucosity, and a red-brown basal leaf sheath color. The selection criterion for 'DT23' was broad leaf width.

Asexual reproduction: The new variety, *Dianella tasmanica* 'DT23', was first asexually propagated by vegetative division in the state of New South Wales, Australia in September 1997 and has been asexually propagated since that time by division and micropropagation. The distinctive characteristics of cultivar 'DT23' have remained stable and true to type through successive cycles of asexual propagation.

SUMMARY OF THE INVENTION

'DT23' is a distinctive variety of *Dianella tasmanica,* which is characterized by its combination of compact form, green leaf color, broad leaf blade width, strong leaf arching, green summer basal leaf sheath color with red-brown margin and large bluish-purple berries.

DETAILED BOTANICAL DESCRIPTION OF THE VARIETY

Figure 1:
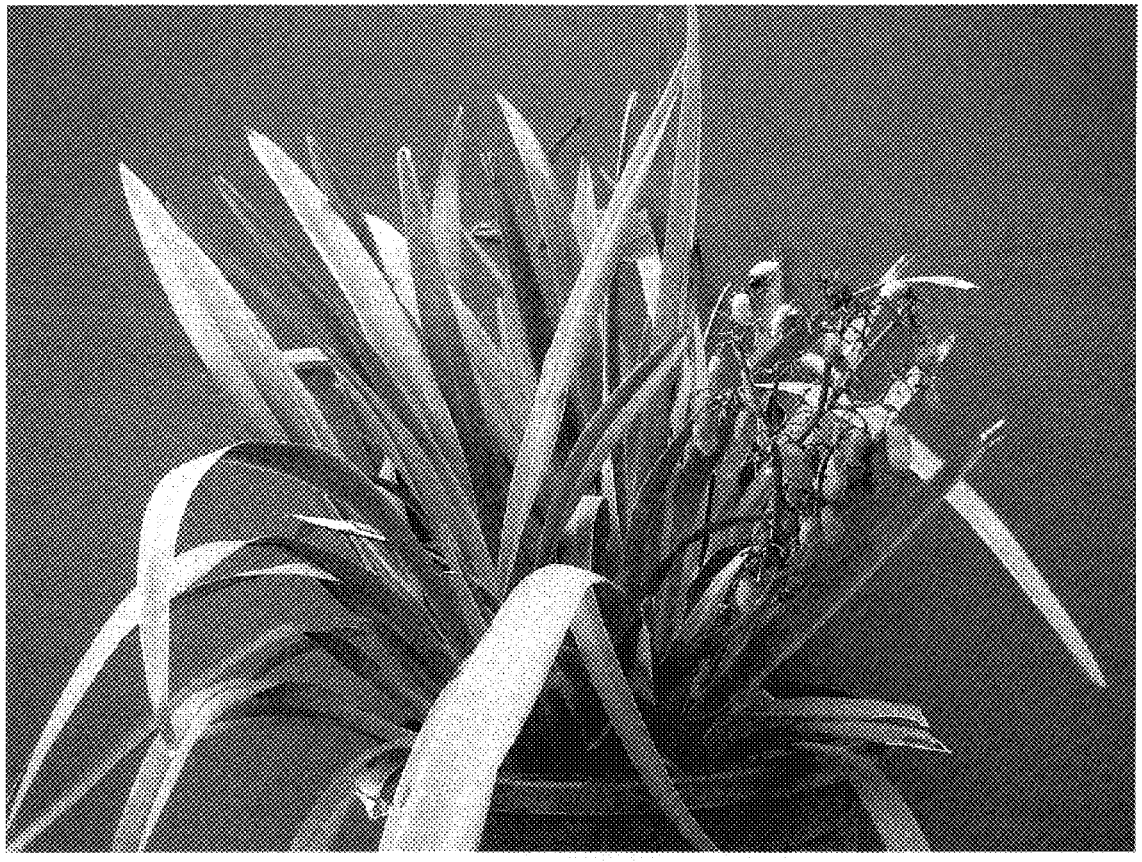
FIG. 1 shows an exemplary *Dianella tasmanica* 'DT23' plant at approximately two years of age.

The following is a detailed botanical description of a new and distinct variety of *Dianella tasmanica* known as 'DT23' based upon observations of 15-month-old plants grown in nursery pots in full sun in open beds in Clarendon, New South Wales, Australia. Color notations are based on The Royal Horticultural Society Colour Chart, The Royal Horticultural Society, London, 1995 Edition.

Those skilled in the art will appreciate that certain characteristics will vary with older or, conversely, with younger plants. 'DT23' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions.

'DT23' is an evergreen perennial *Dianella tasmanica*. 'DT23' is a broad-bladed, compact plant, with strong leaf arching, green leaf color, green summer basal leaf sheath color with red-brown margin and large bluish-purple berries.

A botanical description of 'DT23' and comparisons with other varieties of *Dianella tasmanica* are provided below.

Technical Description of the Variety

Plant characteristics: Growth habit erect to semi-erect, height medium, shoot density medium.

Leaves: Attitude erect to semi-erect, width broad (mean 29 mm), upper side color yellow-green (RHS 147A), lower side color yellow-green (RHS 147B), glaucosity weak, shape ligulate, apex acute, cross-section concave, margin with spines present with medium prominence, midrib lower side with spines present with strong prominence.

Basal sheath: Anthocyanin coloration (summer) red-brown on margin only.

Basal shoots: Attitude erect to semi-erect, arrangement cluster.

Flowers: The flower buds are 8–10 mm long and 3–4 mm wide. Bud color changes from yellow green (RHS 147B) to violet blue (approximately RHS 89A) prior to opening. Mature flowers have 6 petals with ovate shape. Petal color is violet-blue (approximately RHS 94B) in the centre and violet-blue (approximately RHS 97B) at the margin. Anther filament color is yellow (approximately RHS 12A). Flower diameter range is 10–13 mm. Petal attitude is strongly reflexed. Petal length is 8–9 mm and petal width is 3–4 mm. Petal margin is entire and texture is smooth. Petal attachment is sessile with an obtuse to truncate base.

Fruit: A succulent berry, diameter 8–9 mm, length to 20 mm, shape is oblong, color of unripe berry is yellow green (RHS 146A) and color of ripe berry is approximately violet blue (RHS 89A), surface texture is smooth and glossy. Seed color is black.

Cultural conditions: 'DT23' can tolerate low nutrient conditions; it does not like continually wet soil conditions, but can tolerate well-draining sandy soils to very heavy clay soils. 'DT23' is fairly adaptable to a wide range of soil pH.

Cold and heat tolerance: 'DT23' has been observed to be cold tolerant to −12° C. in Clarendon, New South Wales, Australia. Foliage color did not change under these conditions, except for a slight burning at the very tips of the leaves. The plant has also been grown for two years in Charleston, S.C., USA and has remained evergreen down to −6° C.

'DT23' is also very heat tolerant. It adapted well to the high heat conditions during summer in Clarendon, New South Wales, Australia and high heat and humidity conditions during summer in Charleston, S.C., USA without any noticeable disease or insect damage.

Drought tolerance: 'DT23' has very good drought tolerance. 'DT23' survived three months without rainfall under hot conditions in non-irrigated garden beds in summer in Clarendon, Australia. 'DT23' has also been grown in non-irrigated beds in Charleston, S.C., USA for two years, and has been observed to go as long as 30 days without rainfall.

Pest resistance: No known pests.

Figure 2:
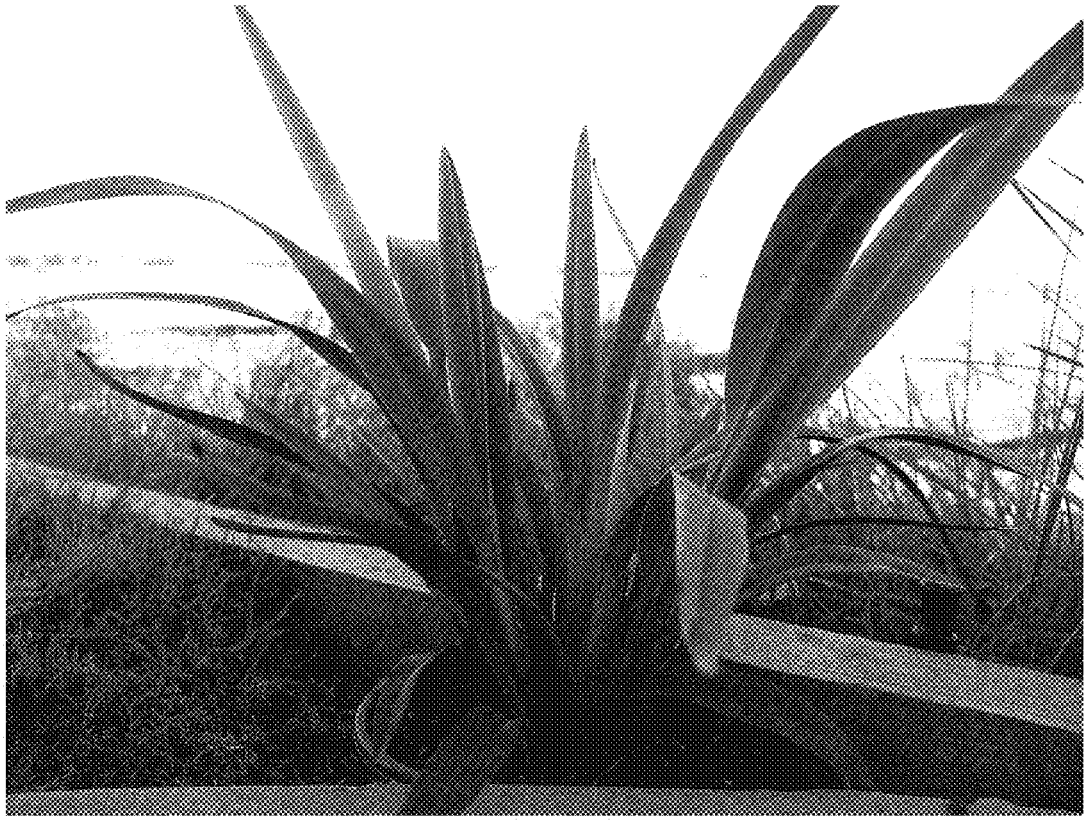
FIG. 2 shows an exemplary *Dianella tasmanica* 'DT23' plant at approximately fifteen months of age.

These and other features and characteristics of 'DT23' are apparent from FIGS. 1 and 2.

Comparisons and other *Dianella*.

'DT23' is a more attractive ornamental glass-like plant as compared with the parent. 'DT23' is characterized by a yellow-green leaf color, broader leaf blade, stronger leaf arching, and the presence of anthocyanin on the basal sheath margin in summer as compared with the parent '*D. tasmanica*' (ecotype from southern tablelands of New South Wales, Australia) (see Table 1).

*Dianella* 'TR20' (U.S. patent application Ser. No. 11/238,477, filed Sep. 29, 2005) is the most similar comparator variety to 'DT23'. In comparison with 'TR20', cultivar 'DT23' has a green leaf color whereas 'TR20' is more yellow-green. 'DT23' has a wider leaf, has stronger leaf arching, and more prominent spines on the lower side midrib than 'TR20'. 'DT23' has a green basal sheath color with a red-brown margin in summer whereas 'TR20' has an overall red-brown basal sheath color (see Table 1).

A comparative trial of *Dianella* cultivar 'DT23' with 'TR20' and the parent *D. tasmanica* was carried out in summer 2003 to autumn 2004 in Clarendon, New South Wales, Australia. Plant observations and descriptions were taken in autumn 2003. The data are presented in Table 1 below. The plants for this trial were propagated from divisions, planted into 130 mm pots filled with soilless potting mix, and moved into 140 mm pots in full sun for nine months before the trial started. Nutrition was maintained with slow release fertilizers; pest and disease treatments were applied as needed. The trial was designed such that twenty plants of each variety were arranged in a completely randomized manner. Measurements were taken from ten plants at random with one sample per plant.

TABLE 1

| | Dianella Variety | | |
|---|---|---|---|
| Characteristic | 'DT23' | 'TR20' | *D. tasmanica* (parent) |
| Plant Height (cm) | | | |
| Mean | 34.2 | 28.0 | 31.5 |
| Std Deviation | 4.5 | 1.9 | 5.7 |
| LSD/Sig. | 4.33 | P ≦ 0.01 | ns* |
| Leaf Width (mm) | | | |
| Mean | 29.1 | 20.0 | 21.3 |
| Std Deviation | 1.6 | 1.7 | 2.0 |
| LSD/Sig. | 1.81 | P ≦ 0.01 | P ≦ 0.01 |
| Leaf Glaucosity | Weak | Absent-very weak | Absent-very weak |
| Leaf lower side midrib: prominence of spines | Strong | Medium | Medium |
| Leaf Color | | | |
| Upper Side | 147A | 146A | 147A |
| Lower Side | 147B | 146B | 147B |
| Basal Sheath Color | Green with red-brown margin | Reddish - brown | Reddish-brown |
| Basal Sheath: intensity of anthocyanin color | Weak | Medium-strong | Medium |

*ns—not significant

That which is claimed is:

1. A new and distinct variety of *Dianella tasmanica* plant named 'DT23', substantially as described and illustrated herein.

* * * * *